United States Patent
Yonezawa

(10) Patent No.: US 6,727,987 B2
(45) Date of Patent: Apr. 27, 2004

(54) IMAGE PICKUP APPARATUS AND DEFECT INSPECTION SYSTEM FOR PHOTOMASK

(75) Inventor: Makoto Yonezawa, Yokohama (JP)

(73) Assignee: Lasertec Corporation, Yokohama (JP)

( * ) Notice: Subject to any disclaimer, the term of this patent is extended or adjusted under 35 U.S.C. 154(b) by 5 days.

(21) Appl. No.: 09/973,780

(22) Filed: Oct. 11, 2001

(65) Prior Publication Data

US 2002/0044277 A1 Apr. 18, 2002

(30) Foreign Application Priority Data

Oct. 18, 2000 (JP) ........................................ 2000-317587

(51) Int. Cl.[7] ............................................... G01N 21/88
(52) U.S. Cl. ................................ 356/237.2; 356/237.4; 356/237.5
(58) Field of Search ................ 356/237.1, 237.2–237.5, 356/239.1–239.8, 432, 445; 250/559.44

(56) References Cited

U.S. PATENT DOCUMENTS

| | | | | |
|---|---|---|---|---|
| 5,075,864 A | * | 12/1991 | Sakai | 701/217 |
| 5,377,004 A | * | 12/1994 | Owen et al. | 356/301 |
| 5,576,829 A | * | 11/1996 | Shiraishi et al. | 356/521 |
| 5,838,433 A | * | 11/1998 | Hagiwara | 356/364 |
| 6,381,356 B1 | * | 4/2002 | Murakami et al. | 382/141 |
| 6,400,454 B1 | * | 6/2002 | Noguchi et al. | 356/237.3 |

* cited by examiner

Primary Examiner—Richard A. Rosenberger
Assistant Examiner—Vincent P Barth
(74) Attorney, Agent, or Firm—Oliff & Berridge, PLC

(57) ABSTRACT

An image pickup apparatus having a higher resolution and S/N ratio by use of a line confocal optical system and a photomask defect inspection system using the same. A first spatial filter having a plurality of slits extending in a direction perpendicular to a direction of movement of a sample is arranged in front of a light source and illuminates the sample with lines of light. The transmitted light or reflected light from the sample is received by an image sensor through a second spatial filter having slits substantially the same as the first spatial filter. Each image sensor has light receiving elements arranged in a two-dimensional array and transfers charges stored in the light receiving elements for each line. A charge transfer speed of the image sensors and speed of movement of the sample are linked with each other. The sample is illuminated a plurality of times, the charge produced by each illumination is accumulated, and the cumulative charge is output. By configuring the apparatus in this way, a line confocal optical system is formed, a greater amount of charge is built up by the illumination by the plurality of lines of light, and the S/N ratio is remarkably improved.

26 Claims, 4 Drawing Sheets

IMAGE PICKUP APPARATUS AND DEFECT INSPECTION SYSTEM FOR PHOTOMASK

BACKGROUND OF THE INVENTION

1. Field of the Invention

The present invention relates to an image pickup apparatus having a high resolution and a high signal-to-noise (S/N) ratio using a confocal optical system.

Further, the present invention relates to a photomask defect inspection system having such an image pickup apparatus.

2. Description of the Related Art

In the process of production of a semiconductor device, a large number of photomasks formed with various different patterns are used. A desired device is manufactured by repeating the steps of pattern transfer and etching on a semi-conductor wafer. When there is a defect in the photomask serving as the master for pattern transfer due to foreign matter etc., an accurate pattern cannot be projected on the semi-conductor wafer and defects end up occurring there. Therefore, there has been a strong demand for improvement of a defect inspection system for detecting a defect of a photomask.

In the past, in a photomask defect inspection system, the photomask to be inspected has been scanned at a high speed by light beam, the light transmitted through or the light reflected from the photomask has been received by a one-dimensional image sensor, and output signals from the image sensor are compared with data stored in a database or compared output signals with each other to detect the presence of foreign matters and the detects of a light blocking pattern.

In an another defect inspection system, the light transmitted through or the light reflected from the photomask is received by a two-dimensional CCD camera, and output signals from the light receiving elements of the CCD camera have been compared with data stored in a database or compared with each other to detect a defect.

Along with the higher integration and higher density of LSIs, the patterns of photomasks have also become finer. There has therefore been a strong demand to further raise the resolution of a photomask defect inspection system and obtain a defect detection signal of a high S/N ratio. The method of receiving the light from the above photomask by a one-dimensional image sensor has the advantage of giving a relatively high resolution since the confocality is maintained. The charge stored in a light receiving element of the image sensor, however, is proportional to the time of irradiation of the illumination light, that is, the time of accumulation of the charge. In the method of high speed scanning using a light beam, the time during which the light from the photomask strikes the image sensor is short, so the amount of charge stored in a light receiving element becomes smaller and there are limits in regard to the S/N ratio of the defect detection signal.

On the other hand, in the method of receiving light from a photomask by a two-dimensional CCD camera, the illumination time can be made relatively longer, so a good characteristic is obtained with respect to the S/N ratio. When picking up a reflected image or transmitted image of the photomask by a two-dimensional CCD camera, flare, glare, and other stray light ends up striking the light receiving elements, there is a limit to the resolution, and there is a limit to the inspection for defects of a fine pattern.

Further, to optically inspect for defects of a fine pattern, it is desirable to use light of a short wavelength, that is, ultraviolet light, as the illumination light. With ultraviolet light, however, since the absorption by the optical elements is large and the sensitivity of the photodiodes is low, there is the disadvantage of difficulty of obtaining a sufficient detection sensitivity with a defect inspection system of the related art. Further, among the types of defects are defects due to the deposition of foreign matter and pattern defects derived from the failure of accurate formation of a chrome light blocking pattern. If these types of defects can be discerned, the applications for defect inspection systems can be further increased.

SUMMARY OF THE INVENTION

An object of the present invention is to provide an image pickup apparatus and photomask defect inspection system able to pick up the image of a sample at a higher resolution than a defect inspection system of the related art and obtain an output signal of a higher S/N ratio.

Another object of the present invention is to provide a defect inspection system able to simultaneously inspect for a defect by transmitted light and inspect for a defect by reflected light and able to discern the properties and details of the detected defect.

According to a first aspect of the present invention, there is provided an image pickup apparatus provided with a sample stage for moving a sample whose image is to be picked up in a first direction; an illumination light source for projecting illumination light on the sample; a first spatial filter arranged between the illumination light source and sample and having a plurality of slits formed at a predetermined pitch along the first direction and extending in a second direction perpendicular to the first direction; an image sensor for receiving reflected light or transmitted light from a sample, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a second spatial filter arranged between the sample stage and the second image sensor and having a plurality of slits formed at a predetermined pitch along the first direction and extending in the second direction; an objective lens arranged between the sample stage and second spatial filter and forming an image of transmitted light or reflected light from the sample on the image sensor via the slits of the second spatial filter; and a drive control circuit for controlling the charge transfer speed of the image sensors and speed of movement of the sample stage; the first and second spatial filters being arranged so that light emitted from the slits of the first spatial filter strikes the sample and the image sensor through the slits of the second spatial filter; the speed of movement of the sample stage and the charge transfer speed of the image sensor being set so that the time interval during which the sample moves from the position which the illumination light passing through an i–th slit of the first spatial filter strikes to the position which the illumination light passing through the adjoining i+1st slit strikes and the time interval during which the charges stored in the line of light receiving elements, of the image sensor, which the light passing through the i–th slit of the second spatial filter strikes are transferred to the line of light receiving elements which the illumination light passing through the adjoining i+1st slit strikes become equal to each other.

In the present invention, since the illumination light is projected as lines of illumination light through a spatial filter having a plurality of slits extending in a direction perpendicular to a direction of movement of the sample and the transmitted light or reflected light from the sample is received at an image sensor through a spatial filter having a plurality of slits extending in a direction perpendicular to the direction of movement of the sample in the same way, a line confocal optical system is formed and as a result it is possible to pick up an image greatly reduced in flare, glare, and other stray light and having a high resolution.

Further, since the speed of movement of the sample and the line transfer speed of the image sensor are made to correspond to each other, that is, since the speed of movement of the sample stage and charge transfer speed of the image sensor are set so that the time during which the sample moves from the position which the illumination light passing through an i–th slit of the first spatial filter strikes to the position which the illumination light passing through the adjoining i+1st slit strikes and the time interval during which the charges stored in the line of light receiving elements, of the image sensor, which the light passing through the i–th slit of the second spatial filter strikes are transferred to the line of light receiving elements which the illumination light passing through the adjoining i+1st slit strikes become equal to each other, the same location of the sample is illuminated a plurality of times and the charges generated due to the plurality of instances of illumination light build up, so the noise can be greatly reduced and the S/N ratio can be greatly improved. As a result, it is possible to simultaneously improve both the resolution and S/N ratio and possible to realize a defect inspection system of a much higher accuracy by using a pickup apparatus having such a high resolution and high S/N ratio as an image pickup optical system of a photomask defect inspection system.

Preferably, the image pickup apparatus is further provided with a position detection device for detecting a position of the sample stage in the first direction, the drive control circuit adjusting a charge transfer speed of the image sensor based on a stage position signal from the position detection device. By adopting such a configuration, the correspondence between the image sensor and stage is maintained even if the speed of movement of the stage shifts from a reference value, a clear image can be picked up at all times, and therefore the accuracy of the detection of defects can be maintained.

According to a second aspect of the present invention, there is provided an image pickup apparatus provided with a sample stage for moving a sample whose image is to be picked up in a first direction; a first light source for projecting illumination light for picking up a transmitted image of a sample; a second light source for projecting illumination light for picking up a reflected image of a sample; a first spatial filter arranged between the first light source and the sample stage and having a plurality of slits formed at a predetermined pitch along the first direction and extending in a second direction perpendicular to the first direction; a second spatial filter arranged between the second light source and the sample stage and having a plurality of slits formed at a predetermined pitch along the first direction and extending in the second direction perpendicular to the first direction; a first image sensor for receiving light generated from the first light source and passing through the sample, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a second image sensor for receiving light generated from the second light source and reflected at the sample, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a third spatial filter arranged between the sample stage and first image sensor and having a plurality of slits formed at a predetermined pitch along the first direction and extending in the second direction; a fourth spatial filter arranged between the sample stage and second image sensor and having a plurality of slits formed at a predetermined pitch along the first direction and extending in the second direction; an object lens arranged between the sample stage and third and fourth spatial filters and forming an image of transmitted light and reflected light from the sample on the first and second image sensors via the slits of the third and fourth spatial filters; and a drive control circuit for controlling the charge transfer speed of the first and second image sensors and speed of movement of the sample stage; the first spatial filter and third spatial filter being arranged so that illumination light emitted from the slits of the first spatial filter strike the sample, object lens, and image sensor through the slits of the third spatial filter; the second spatial filter and fourth spatial filter being arranged so that illumination light emitted from the slits of the second spatial filter strike the sample, object lens, and image sensor through the slits of the fourth spatial filter; the speed of movement of the sample stage and the charge transfer speed of the first and second image sensors being set so that the time during which the sample moves from the position which the illumination light passing through an i–th slits of the first and second spatial filters strikes to the position which the illumination light passing through the adjoining i–1st slits strikes and the time during which the charges stored in the line of light receiving elements, of the image sensors, which the light passing through the i–th slits of the third and fourth spatial filters strikes are transferred to the line of light receiving elements which the illumination light passing through the adjoining i+1st slits strikes become equal to each other.

This image pickup apparatus can simultaneously pick up a reflected image and transmitted image of the sample. In this image pickup apparatus, by making the wavelength of the transmitted illumination light and the wavelength of the reflected illumination light different each other and arranging a dichroic mirror between the sample and image sensors 1, it is possible to easily separate the transmitted light and reflected light from the sample each other. When this image pickup apparatus is used for inspection of defects in a photomask, output signals of the first and second image sensors are supplied to a defect detection circuit, the output signals of the two image sensors are added, and the resultant output signal is compared with a threshold value by a comparison circuit to detect the presence of foreign matter.

Preferably, the first and second light sources generate illumination light of equal wavelengths and the third and fourth spatial filters are arranged so that the transmitted light from the sample strikes the light blocking portions between slits of the fourth spatial filter and the reflected light from the sample strikes the light blocking portions between the slits of the third spatial filter.

Preferably, the wavelength of the illumination light generated from the first light source and the wavelength of the illumination light generated from the second light source are made different from each other and a separation element for separating the transmitted light and reflected fight from the sample is arranged between the sample and the third and fourth spatial filters.

According to a third aspect of the present invention, there is provided an image pickup apparatus provided with a sample stage for moving a sample whose image is to be picked up in a first direction; a light source for generating a light beam; a diffraction grating for generating n number of sub beams at predetermined intervals along a direction corresponding to the first direction from the light beam; a beam deflection device for cyclically deflecting the sub beams by a predetermined frequency in a second direction perpendicular to the first direction; an image sensor for receiving reflected light or transmitted light from a sample, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a spatial filter arranged between the sample stage and image sensor and having a plurality of slits formed at a predetermined pitch along the first direction and extending in the second direction; an object lens arranged forming an image of transmitted light or reflected light from the sample on the image sensor via the slits of the second spatial filter; and a drive control circuit for controlling the drive of the image sensor and beam deflection apparatus; the reflected light or transmitted light due to the plurality of sub beams scanning the surface of the sample striking the image sensor through the slits of the spatial filter; the speed of movement of the sample stage and the charge transfer speed of the image sensor being set so that the time interval during which the sample moves from the position which an i–th sub beam strikes to the position which the adjoining i+1st sub beam strikes and the time interval during which the charges stored in the line of light receiving elements, of the image sensor, which the light passing through the i–th slit of the spatial filter strikes are transferred to the line of light receiving elements which the illumination light passing through the adjoining i+1st slit strikes become equal to each other.

In this way, since a confocal optical system is formed by using multi beam illumination and the sample is illuminated a plurality of times, a sample having a high resolution and high S/N ratio can be picked up. Therefore, by using an image pickup apparatus as an image pickup optical system of a photomask defect inspection system, it is possible to detect defects of a photomask by a higher solution and higher S/N ratio.

According to a fourth aspect of the present invention, there is provided an image pickup apparatus provided with a sample stage for moving a sample whose image is to be picked up in a first direction; a light source for generating illumination light for picking up a transmitted image; a first spatial filter arranged between the illumination light source and sample and having a plurality of slits formed at a predetermined pitch along the first direction and extending in a second direction perpendicular to the first direction; a first image sensor for receiving transmitted light from a sample, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a second spatial filter arranged between the sample and first image sensor and having a plurality of slits formed at a predetermined pitch along the first direction and extending in the second direction; a light source for generating a light beam for picking up a reflected image; a diffraction grating for generating n number of sub beams from the light beam; a beam deflection device for deflecting the sub beams by a predetermined frequency in a second direction perpendicular to the first direction; a second image sensor for receiving reflected light from a sample, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a third spatial filter arranged between the sample stage and second image sensor and having a plurality of slits formed at a predetermined pitch along the first direction and extending in the second direction; an objective lens arranged forming an image of transmitted light and reflected light from the sample on the image sensors via the slits of the second and third spatial filters; and a drive control circuit for controlling the drive of the first and second image sensors and beam deflection apparatus; the first and second spatial filters being arranged so that light emitted from the slits of the first spatial filter strike the sample, the object lens, and the first image sensor through the slits of the second spatial filter; the third spatial filter being arranged so that reflected light from the sample strikes the objective lens and the second image sensor through the slits of the third spatial filter; the speed of movement of the sample stage and the charge transfer speed of the image sensors being set so that the time during which the sample moves from the position which the i-th sub beam strikes to the position which the adjoining i+1st sub beam strikes and the time during which the charges stored in the line of light receiving elements, of the image sensors, which the light passing through the i–th slit of the spatial filter strikes is transferred to the line of light receiving elements which the illumination light passing through the adjoining i+1st slit strikes become equal to each other. In this embodiment, the reflected image pickup optical system and transmitted image pickup optical system are formed by confocal optical systems, so a high resolution high S/N ratio image can be picked up.

According to a fifth aspect of the present invention, there is provided an image pickup apparatus provided with a sample stage for moving a sample whose image is to be picked up in a first direction; an illumination light source for projecting illumination light for picking up a transmitted image; a first spatial filter arranged between the illumination light source and sample and having a plurality of slits formed at a predetermined pitch along the first direction and extending in a second direction perpendicular to the first direction; a first image sensor for receiving transmitted light from a sample, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a second spatial filter arranged between the sample and first image sensor and having a plurality of slits formed at a predetermined pitch along the first direction and extending in the second direction; a light source for generating a light beam for picking up a reflected image; a beam deflection apparatus for deflecting the light beam by a predetermined frequency in a second direction perpendicular to the first direction; a linear image sensor for receiving reflected light from the sample, having a plurality of light receiving elements arranged in a line along the second direction, and reading out the charges stored in the light receiving elements in synchronization with the first image sensor; an objective lens arranged for forming an image of transmitted light and reflected light from the sample on the first image sensor and linear image sensor; and a drive control circuit for controlling the drive of the first and linear image sensors and the beam deflection apparatus; the first and second spatial filters being arranged so that light emitted from the slits of the first spatial filter strike the sample, the object lens, and the image sensor through the slits of the second spatial filter; the speed of movement of the sample stage and the charge transfer speed of the image sensors being set so that the time during which the sample moves from the position which the i–th sub beam strikes to the position which the adjoining i+1st sub beam strikes and the time during which the charges stored in the line of light receiving elements, of the image sensors, which the light passing through the i–th slit of the spatial filters strikes are transferred to the line of light receiving elements which the illumination light passing through the adjoining i+1st slit strikes become equal to each other. By this defect inspection system, it is possible to detect a defect of a photomask by a die-to-die or chip-to-chip relationship. It is therefore possible to defect fine defects at a high speed and with a high accuracy.

Preferably, the beam deflection apparatus is comprised by an acoustic optical element and the beam deflection frequency of the acoustic optical element is set to a whole multiple (including an equal value) of the charge transfer speed of the image sensors.

More preferably, each light receiving element of the image sensors has a charge storing ability able to store a charge generated in accordance with light striking it.

In accordance with a sixth aspect of the present invention, there is provided a photomask defect inspection system provided with a stage for moving a photomask to be inspected for defects in a first direction; an illumination light source for projecting illumination light on the photomask; a first spatial filter arranged between the illumination light source and stage and having a plurality of slits formed at a predetermined pitch along the first direction and extending in a second direction perpendicular to the first direction; a first image sensor for receiving transmitted light from the photomask, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a second spatial filter arranged between the stage and first image sensor and having a plurality of slits formed at a predetermined pitch along the first direction and extending in the second direction; a light source for generating a light beam for picking up a reflected image; a diffraction grating for generating n number of sub beams from the light beam at equal intervals along a direction corresponding to the first direction; a beam deflection apparatus for cyclically deflecting the sub beams by a predetermined frequency in a second direction perpendicular to the first direction; a second image sensor for receiving reflected light from the photomask, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a third spatial filter arranged between the stage and second image sensor and having a plurality of slits extending in the second direction; an object lens for forming an image of transmitted light and reflected light from the sample on the first and second image sensors via the slits of the second and third spatial filters; a drive control circuit for controlling the drive of the first and second image sensors and the beam deflection apparatus; and a defect detection circuit for detecting defects of the photomask based on the output signals of the first and second image sensors; the first and second spatial filters being arranged so that the light emitted from the slits of the first spatial filter enter the slits of the second spatial filter; the third spatial filter being arranged so that the reflected light of the plurality of sub beams scanning the surface of the photomask enter the slits of the third spatial filter; the charge transfer speed of the first and second image sensors and the speed of movement of the stage being set so that the time interval during which the sample moves from the position which the i–th sub beam strikes to the position which the adjoining i+1st sub beam strikes and the time interval during which the charges stored in the line of light receiving elements, of the image sensor, which the light passing through the i–th slit of the spatial filter strikes are transferred to the line-of light receiving elements which the illumination light passing through the adjoining i+1st slit strikes become equal to each other.

According to a seventh aspect of the present invention, there is provided a photomask defect inspection system provided with a stage for moving a photomask to be inspected for defects in a first direction, first and second image pickup apparatuses for picking up an image of the photomask, and a defect detection circuit for detecting defects existing in a photomask based on output signals of the first and second image pickup apparatuses; each of the first and second image pickup apparatuses being provided with an illumination light source for projecting illumination light on the photomask; a first spatial filter arranged between the illumination light source and stage and having a plurality of slits formed at a predetermined pitch along the first direction and extending in a second direction perpendicular to the first direction; a first image sensor for receiving transmitted light from the photomask, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a second spatial filter arranged between the stage and first image sensor and having a plurality of slits formed at a predetermined pitch along the first direction and extending in the second direction; a light source for generating a light beam for picking up a reflected image; a diffraction grating for generating n number of sub beams from the light beam at equal intervals along a direction corresponding to the first direction; a beam deflection apparatus for cyclically deflecting the sub beams by a predetermined frequency in a second direction perpendicular to the first direction; a second image sensor for receiving reflected light from the photomask, having a plurality of light receiving elements arranged in a two-dimensional array along the first and second directions, successively transferring the charges stored in one line of light receiving elements arranged in the second direction for each line at a predetermined transfer speed, and successively outputting the charges stored in the light receiving elements; a third spatial filter arranged between the stage and second image sensor and having a plurality of slits extending in the second direction; an object lens for forming an image of transmitted light and reflected light from the sample on the first and second image sensors via the slits of the second and third spatial filters; and a drive control circuit for controlling the drive of the first and second image sensors and the beam deflection apparatus; the first and second spatial filters being arranged so that the light emitted from the slits of the first spatial filter enter the slits of the second spatial filter; the third spatial filter being arranged so that the reflected light of the plurality of sub beams scanning the surface of the photomask enter the slits of the third spatial filter; the charge transfer speed of the first and second image sensors and the speed of movement of the stage being set so that the time interval during which the sample moves from the position which the i–th sub beam strikes to the position which the adjoining i+1st sub beam strikes and the time interval during which the charges stored in the line of light receiving elements, of each image sensor, which the light passing through the i–th slit of the spatial filter strikes are transferred to the line of light receiving elements which the illumination light passing through the adjoining i+1st slit strikes become equal to each other.

Preferably, the defect detection circuit is provided with a comparison circuit for comparing output signals of the first and second image sensors of the first image pickup apparatus and output signals of the first and second image sensors of the second image pickup apparatus and defects are detected based on the results of the comparison circuit.

BRIEF DESCRIPTION OF THE DRAWINGS

These and other objects and features of the present invention will become clearer from the following description of the preferred embodiments given with reference to the attached drawings, wherein.

DESCRIPTION OF THE PREFERRED EMBODIMENTS

Preferred embodiments of the present invention will be described in detail below while referring to the attached figures.

Figure 1:
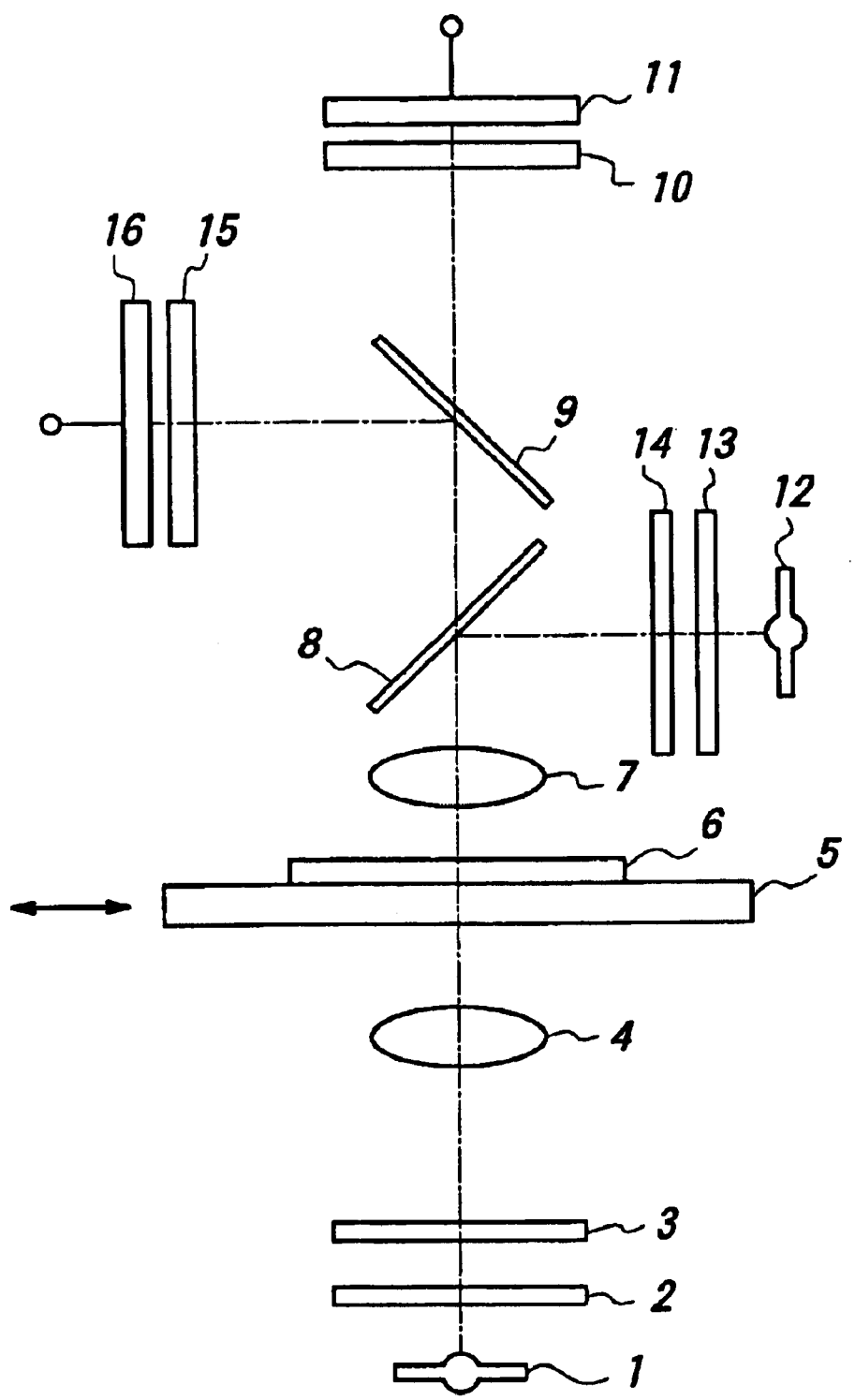
FIG. 1 is a line drawing showing the configuration of an example of an image pickup apparatus and photomask defect inspection system according to the present invention.

FIG. 1 is diagrammatically shows the configuration of one example of an image pickup apparatus and a photomask defect inspection system according to the present invention. In this example, an explanation will be made of a system able to individually or simultaneously inspect by transmission type and reflection type systems. For example, a first light source 1 such as a mercury lamp is used as the illumination light source, a wavelength filter 2 passing only light of a wavelength of 365 nm is arranged in front of the first light source 1, and a first spatial filter 3 is arranged after that. The spatial filter is formed at a predetermined pitch with a plurality of slits extending in a direction perpendicular to the paper surface, that is, a first direction. The lines of illumination light passing through the slits of the spatial filter 3 pass through an illumination lens 4 and strike a sample 6 supported on a sample stage 5 as parallel light beams. In this example, the sample 6 is a photomask comprised of a transparent substrate formed with a chrome light blocking pattern. The sample stage 5 moves at a predetermined speed in the direction of the arrows, that is, a second direction perpendicular to the direction of extension of the slits of the spatial filter 3. Therefore, the photomask 6 is illuminated a plurality of times by the plurality of lines of illumination light.

The lines of illumination light passing through the photomask 6 pass through an objective lens 7 and first and second half mirrors 8 and 9 and pass through a second spatial filter 10 to strike a first image sensor 11. The second spatial filter 10 is arranged in front of a first image sensor 11 and is formed at a predetermined pitch with a plurality of slits extending in the first direction perpendicular to the paper surface in the same way as the filter spatial filter 3. Further, the second spatial filter 10 is arranged so that the lines of transmission light passing through the slits of the first spatial filter 3 and passing through the photomask pass through the slits. The first image sensor 11 is an image sensor having a plurality of light receiving elements arranged in a two-dimensional array in the first and second directions. In this example, 2048 light receiving elements are arranged in the first direction and 140 lines of light receiving elements in the second direction. The second direction will be called the "line direction". Therefore, the image sensor 11 is formed with 2048 light receiving elements in a line and has 140 lines of light receiving elements. The first spatial filter 3, photomask 6, and first image sensor 11 are arranged in a conjugate relationship. Therefore, images of the slits of the first spatial filter are projected on the photomask 6, while the transmitted image of the photomask is projected on the first image sensor 11 by the object lens 7. By configuring the apparatus in this way, a line confocal optical system is formed and the resolution can be increased more. Further, it is possible to use a so-called TDI line sensor comprised of an image sensor and spatial filter formed integrally and designed so that light strikes only the light receiving elements of specific lines.

To pick up a reflected image of the photomask 6, a second light source 12 is provided, a wavelength filter 13 passing only light of a wavelength of 365 nm is arranged in front of the second light source, and a third spatial filter 14 is arranged after the wavelength filter. In this example, the second light source 12 is comprised by a light source identical to the first light source. The third spatial filter 14, like the first spatial filter, is also a spatial filter formed at a predetermined pitch with a plurality of slits extending in a direction perpendicular to the paper surface, that is, the first direction. The lines of illumination light produced from the second light source 12 and passed through the slits of the third spatial filter 14 are reflected at the first half mirror 8, pass through the object lens 7, and strike the photomask 6. Therefore, the photomask 6 is scanned a plurality of times by the plurality of lines of illumination light extending in a direction perpendicular to the direction of movement. The lines of light reflected at the photomask 6 again pass through the object lens 7, pass through the first half mirror 8, are reflected at the second half mirror 9, pass through a fourth spatial filter 15, and strike a second image sensor 16. The fourth spatial filter 15 and second image sensor 16 are configured identically to the second spatial filter 10 and first image sensor 11, respectively. The fourth spatial filter 15 is arranged so that the respective line of light passing through the slits of the corresponding third spatial filter 14 and reflected at the photomask 6 pass through each slit, respectively. Therefore, a confocal optical system is formed for the reflected image pickup optical system and it is possible to pick up an image with a higher resolution reduced in influence of stray light. Further, the third spatial filter 14 arranged in front of the second light source for use of reflection type, is arranged so that the lines of reflected light passing through the slits and reflected at the photomask 6 strike the light blocking portions between the slits of the second spatial filter 10 for picking up the transmitted light, that is, so that they do not strike the first image sensor and strike only the second image sensor 16. By configuring the system in this way, it is possible to individually pick up the transmitted image and reflected image of the photomask 6. Further, by using image sensors of the same structure, for example, the above TD1 sensors, for the first and second image sensors, it is possible to eliminate the disadvantages derived from the differences in structure in the image sensors and therefore the problem of asynchronization between the transmitted image and reflected image for example is eliminated.

Further, for image signals, it is possible to use as image signals the output signals of the first and second image sensors 11 and 16 or to route the outputs of the image sensors through a scan converter and use the output signals as image signals. Further, when using this image pickup apparatus for detecting defects, it is possible to supply the outputs of the first and second image sensors to a defect detection circuit and process the signals in the defect detection circuit to detect defects of the photomask. For example, by supplying the output of the first image sensor 11 and the output of the second image sensor 16 to an adder and comparing the output of the adder with a threshold value by a comparison circuit, it is possible to detect the existence of foreign matter deposited on the surface of the photomask.

It is also possible to arrange wavelength filters of different transmitted wavelength bands in front of the first and second light sources 1 and 12 to make the wavelength of the illumination light for picking up the transmitted image and the wavelength of the illumination light for picking up the reflected light different from each other. In this case, instead of the half mirror 9, a dichroic mirror for separating the reflected light and transmitted light from the sample is used. By making the, wavelengths of the illumination light different in this way, the reflected image and transmitted image can be easily separated.

Further, in the first embodiment, two mercury lamps were used for picking up the transmitted image and picking up the reflected image, but it is also possible to use a single mercury lamp as the light source, split the light from the mercury lamp into two luminous fluxes using two optical fibers, and use the luminous fluxes for picking up the transmitted image and picking up the reflected image. In this case, there is the advantage that the fluctuation in the intensity of the output of the light source is canceled between transmission and reflection.

Figure 2:
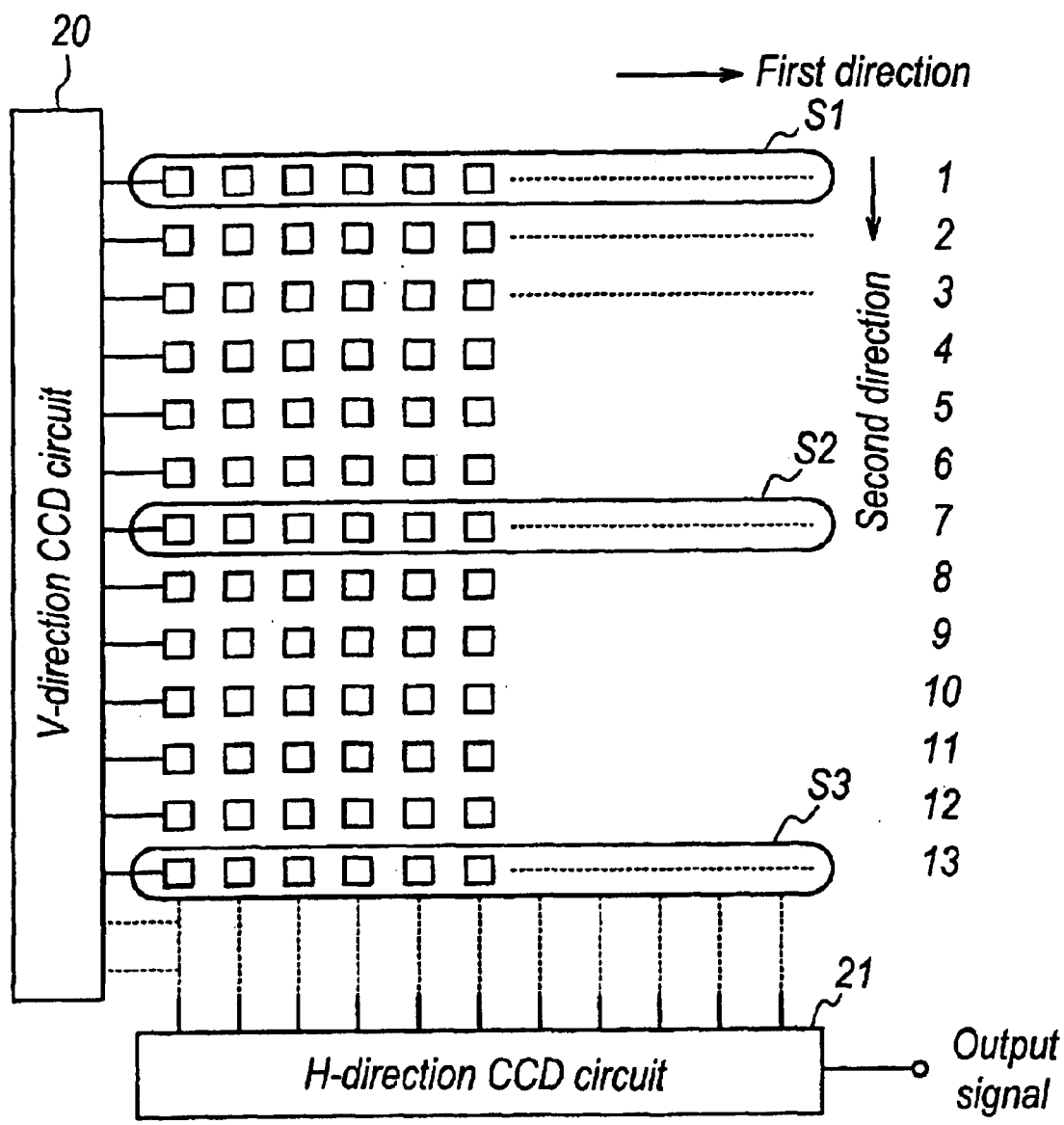
FIG. 2 is a line drawing showing the relationship between an image sensor and a spatial filter.

Next, an explanation will be given of the relationship between an image sensor and a spatial filter arranged in front of it. FIG. 2 diagrammatically shows the relationship between an array of light receiving elements of the first image sensor and the array of slits of the second spatial filter arranged in front of it. The image sensor has 2048 light receiving elements arranged along a direction corresponding to the first direction to form a first line and has 140 lines of light receiving elements arranged in a second direction perpendicular to the first direction. The slits S1 to Sn of the spatial filter are arranged every six lines, that is, on the first line, seventh line, 13th line, etc. of the image sensor. Therefore, the transmitted light or reflected light from the sample, that is, the photomask, strikes only the light receiving elements of the first line, seventh line, 13th line . . . (6m+1) . . . th line of the image sensor. Therefore, the light strikes only the light receiving elements of the 6m+1st lines of light receiving elements. The light receiving elements positioned between the above line of light receiving elements function to transfer the transferred charges to the next lines of light receiving elements. The image sensor has a V-direction CCD circuit 20 and H-direction CCD circuit 21 connected thereto. The charges occurring at the lines of light receiving elements are successively transferred to the next light receiving elements for each line under the control of the V-direction CCD circuit 30, while the charges accumulated at the lines of light receiving elements are successively serially output under the drive control of the H-direction CCD circuit 21.

In the present invention, the speed of movement of the sample stage and the speed of transfer in the V-direction (corresponding to second direction) of the image sensor are made to correspond to each other. That is, the time interval after the sample passes the i-th slits of the spatial filters 3, 13 to when it reaches the adjoining i+1st slits and the time interval until the charges stored in the lines of light receiving elements corresponding to the i-th slits of the spatial filters 10 and 15 of the light receiving side are transferred to the adjoining lines of light receiving elements corresponding to the i+1 th slits are set to be equal to each other. By configuring the system in this way, the equivalent effect is obtained as if the sample were scanned a plurality of times by lines of illumination light. On the other hand, since the light receiving elements of the image sensors have a charge storing ability, the charges produced by each scans successively build up. As a result, the noise occurring at the light receiving elements etc. can be greatly reduced and a signal with a high S/N ratio and high sensitivity can be output. Further, since the charge storing ability of the light receiving elements is positively utilized, even if ultraviolet light with a high absorption at light receiving elements is used, it is possible to produce output signals with a high output level and high sensitivity.

Figure 3:
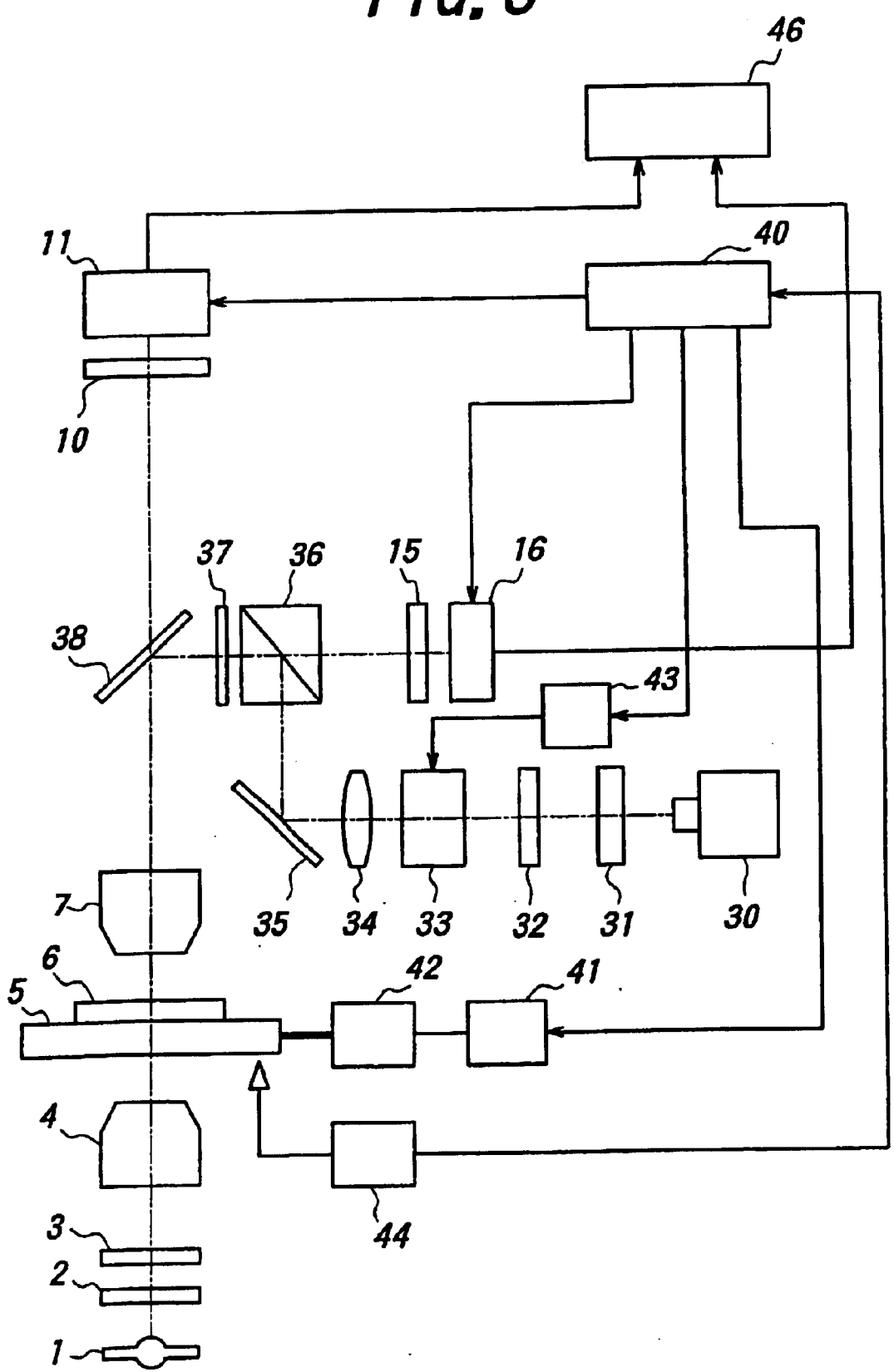
FIG. 3 is a line drawing showing the configuration of another embodiment of an image pickup apparatus and photomask defect inspection system according to the present invention.

FIG. 3 is diagrammatically shows another embodiment of the image pickup apparatus and photomask defect inspection system according to the present invention. In this example, as the reflection type image pickup optical system, use is made of a combination of a laser light source, diffraction grating, and beam deflection device instead of a combination of light source and spatial filters. Further, members the same as the members used in FIG. 1 are assigned the same reference numerals and explanations thereof are omitted. As the light source of the reflection type image pickup apparatus, for example an argon laser 30 generating a light beam of a wavelength of 488 nm is used. The laser beam emitted from this argon laser 30 is converted into expanded parallel luminous flux by an expander 31, which is then passed through a diffraction grating 32 to generate n number of sub beams separated by equal intervals in a direction corresponding to the direction of movement of the sample, that is, the second direction. The number of sub beams is preferably made to correspond to the number of slits of the second spatial filter 15 arranged in front of the second image sensor 16 for receiving the reflected light. These n number of sub beams strike an acoustic optical element 33 and pass through a relay lens 34 and are deflected by a predetermined deflection frequency in the first direction. The deflection frequency of the acoustic optical element does not necessarily have to be equal to the line transfer frequency of the image sensor 16, but is preferably set to a whole multiple (including equal value) of the line transfer frequency of the image sensor 16.

The sub beams travel via the full reflection mirror 35, polarization beam splitter 36, and ¼ wavelength plate 37 and then strike the dichroic mirror 38. In this example, for picking up the transmitted light, a wavelength filter 2 passing light of a wavelength of 365 nm is arranged in front of the light source 1, so the dichroic mirror 38 is used to separate the transmitted light and reflected light from the sample. The n number of sub beams of the wavelength 488 nm are reflected by the dichroic mirror 38 and strike the sample, that is, the photomask 6, focused to spots through the object lens 7. Therefore, a plurality of light spots separated by equal intervals at a predetermined pitch are formed on the photomask 6 along the direction of movement of the photomask, that is, the second direction. The sample 6 is scanned by these light spots at a high speed in a first direction perpendicular to the direction of movement of the photomask. Therefore, each location of the photomask is scanned n number of times by the n number of light beams.

The reflected light from the surface of the sample 6 travels via the object lens 7, is reflected at the dichroic mirror 38, passes through the ¼ wavelength plate 37, then strikes the polarization beam splitter 36. The reflected light passes through the ¼ wavelength plate two times, so the polarization plane is rotated 90 degrees. Therefore, the reflected light passes through the deflection beam splitter 36 and strikes the second spatial filter 15. Here, the optical elements of the reflection optical system are set so that the reflected light from the light spots formed on the sample strike the slits of the spatial filter 15. Therefore the slits of the spatial filter 15 are scanned by the reflected light oscillating in the second direction. The reflected light passes through the slits and strikes lines of light receiving elements of the second image sensor 16 arranged after this. That is, the lines of light receiving elements of the second image sensor corresponding to the slits of the spatial filter 15 are scanned by the sub beams deflected by the acoustic optical element 4333.

Next, an explanation will be given of the drive control of the image pickup apparatus. For drive control, a synchronization signal generation circuit 40 is provided. The apparatuses are controlled based on the drive signals transmitted from the synchronization signal generation circuit. A stage feed pulse is supplied from the synchronization signal generation circuit 40 to the motor driver 41. The stage drive motor 42 is driven by the drive signal from the motor driver 41 to drive the sample stage 5 in the first and second directions.

Line shift pulses are supplied from the synchronization signal generation circuit 40 to the first and second image sensors 11 and 16. Charges stored in the light receiving elements are successively transferred and serially output for each line at a line transfer speed of for example 40 kHz. Further, drive pulses of 40 kHz are supplied from the synchronization signal generation circuit 40 to an acoustic optical element control circuit 43 controlling the drive of the acoustic optical element 33. The acoustic optical element 33 is controlled by the same frequency as the line transfer speed of the image sensor. Therefore, when scanning by n number of sub beams, the sample and light receiving elements are scanned n number of times.

In the present invention, it is necessary to accurately synchronize the speed of movement of the sample and the line transfer speed of the image sensors. Therefore, in this example, a stage position detection apparatus 44 such as a laser interferometer is used to detect the position of the sample stage 45 and the result is supplied to the synchronization signal generation circuit 40. In the synchronization signal generation circuit, the frequency of the line shift pulses for the image sensors is corrected in accordance with the detected position of the sample stage so that the line transfer speed of the image sensors and the speed of movement of the sample stage correspond. By using such a feedback system, even if a slight error in speed occurs in the movement of the stage, it is possible to make the transfer speed of the image sensors and the speed of movement of the stage accurately correspond.

Further, when using the image pickup apparatus shown in FIG. 3 to detect defects, as explained in FIG. 1, it is possible to supply the outputs of the first and second image sensors to a defect detection circuit 46, use an adder to generate a sum signal of the output signals of the image sensors, and compare the sum signal with a threshold value to detect the existence of foreign matter.

Further, in the embodiment shown in FIG. 3, to pick up the reflected image, it is possible to scan using a single light beam rather than using the diffraction grating 32. That is, it is also possible to pick up both the reflected image and transmitted image using a combination of spatial filters and a two-dimensional image sensor for one of the reflected image and transmitted image and one scanning beam and a linear image sensor for the other image.

Figure 4:
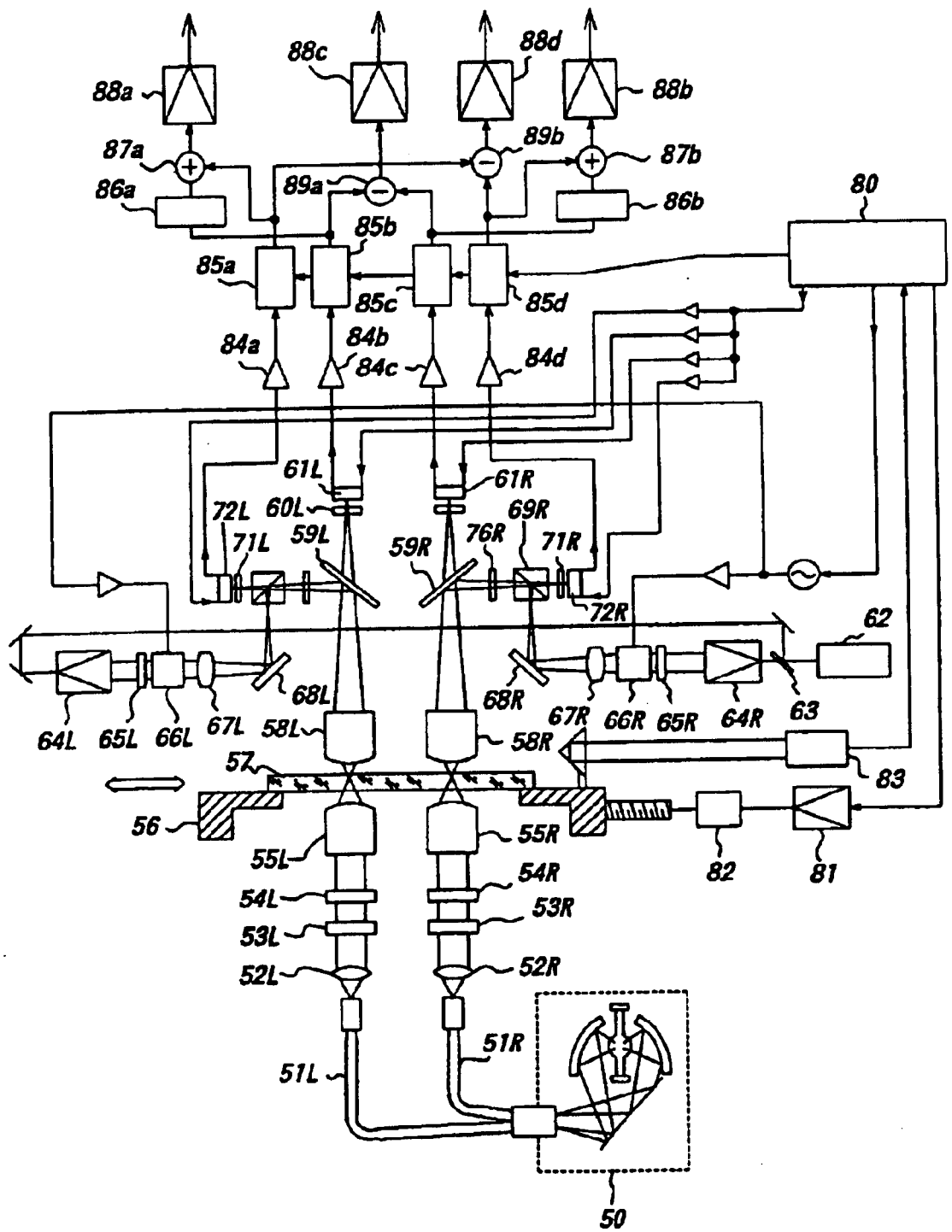
FIG. 4 is a line drawing showing the configuration of an example of a photomask defect inspection system of the present invention using a die-to-die inspection system.

FIG. 4 shows an embodiment applying the image pickup apparatus shown in FIG. 3 to a photomask defect inspection system. In this example, the explanation will be made of an example of using two image pickup heads to detect defects by die-to-die comparison. Most photomasks are formed with a plurality of the same dies, that is, chips, so it is possible to detect defects by using two image pickup heads of the same configuration to pick up the images of two adjoining mask patterns by a die-to-die or chip-to-chip relationship and comparing the results.

In this explanation, the suffixes L and R are given to members of the left side and right side image pickup heads of the same optical element. Illumination light for picking up the transmitted light is generated from a mercury lamp 50. This illumination light is split into two luminous fluxes using the two optical fibers 51L and 51R. These illumination light travel via the lenses 52L and 52R, the wavelength filters 53L and 53R passing light of the wavelength of 365 nm, the first spatial filters 54L and 54R, and the condenser lenses 55L and 55R to strike the sample placed on the stage 56, that is, the photomask 57, as a plurality of line-shaped beams.

The beams of illumination light passing through the photomask 57 are condensed by the objective lenses 58L and 58R, pass through the dichroic mirrors 59L and 59R, and pass through the slits of the second spatial filters 60L and 60R to strike the first image sensors 61L and 61R.

To pick up the reflected image, use is made of an argon laser 62 generating a light beam of a wavelength of 488 nm. The light generated from the argon laser is split into two beams using a half mirror 63. One of the light beams is used for the right side image pickup head, while the other of the light beams is used for the left side image pickup head. The light beam passing through the half mirror 63 passes through an expander 64R of the right side head to strike a diffraction grating 65 where it is converted to a plurality of sub beams. These sub beams scan the photomask at a high speed in a direction perpendicular to the direction of movement of the photomask by the acoustic optical element 66R. These sub beams travel via a full reflection mirror 68R and strike a polarization beam splitter 69R, are reflected at the deflection plane, pass through a ¼ wavelength plate 70R, and strike a dichroic mirror 59R. The beams are reflected at the dichroic filter mirror, are condensed into spots by an objective lens 58R, strike the photomask 57, form n number of light spots at equal intervals in the direction of movement of the photomask, and scan the surface of the photomask in a direction perpendicular to the direction of movement at a high speed.

The sub beams reflected at the photomask again travel via the objective lens 58R, are reflected at the dichroic mirror 59R, and travel via the ¼ wavelength plate 70R, deflection beam splitter 69R, and third spatial filter 71R to strike the second image sensor 72R picking up the reflected image.

For the reflected image pickup optical system of the left side image pickup head, the optical system from an expander 64L to a second image sensor 72L is configured the same as the right side head, so an explanation thereof will be omitted.

Next, an explanation will be made of the drive control of this image pickup optical system. For drive control, a synchronization signal generation circuit 80 is provided. The drive apparatuses are controlled based on the drive signals transmitted from the synchronization signal generation circuit. Stage feed pulses are supplied from the synchronization signal generation circuit 80 to a motor driver 81. A stage drive motor 82 is driven by the drive signal from the motor driver 81 to drive the stage 56 in the first and second directions.

Line shift pulses are supplied from the synchronization signal generation circuit 80 to the first and second image sensors 61L, 61R, 72L, and 72R of the left side and right side heads. Charges stored in the light receiving elements are successively transferred and serially output for each line at a line transfer speed of for example 40 kHz. Further, drive pulses of 40 kHz are supplied from the synchronization signal generation circuit 80 to acoustic optical element control circuits controlling the drive of the acoustic optical elements 66L and 66R. The acoustic optical elements 66L and 66R are controlled by the same frequency as the line transfer speed of the image sensors. Therefore, when scanning by n number of sub beams, the sample and light receiving elements are scanned n number of times.

Further, a stage position detection apparatus 83 such as a laser interferometer is used to detect the position of the sample stage 56 and the result is supplied to the synchronization signal generation circuit 80. In the synchronization signal generation circuit, the frequency of the line shift pulses for the image sensors is corrected in accordance with the detected position of the sample stage so that the line transfer speed of the image sensors and the speed of movement of the sample stage correspond.

Next, an explanation will be made of the defect inspection circuit. The output signals from the first and second image sensors 61L, 61R and 72L, 72R of the left side image pickup head and right side image pickup head are amplified by amplifiers 84*a* to 84*d* and supplied to the scan converters 85*a* to 85*d*. The line shift pulses are supplied from the synchronization signal generator 80 to the scan converters where they are converted to serial output signals and supplied to the defect detection circuit. The signals output from the first image sensors 61L and 61R of the left side and right side heads and passing through the scan converters 85*b* and 85*c* are supplied to thickness adjustment circuits 86*a* and 86*b* where the thickness of the transmitted image is adjusted to match with the thickness of the reflected image, then are supplied to the adders 87*a* and 87*b*. The output signals from the scan converters 84*a* and 84*d* expressing the reflected image are supplied to the other inputs of the adders. Further, the signals of the transmitted image and the signals of the reflected image are added and supplied to first and second differential amplifiers 88*a* and 88*b* where the output signals of the adders are compared with the threshold value. When there is no foreign matter on the surface of the photomask, the sum of the output of the transmitted image and the output of the reflected image becomes substantially a constant value at all times. On the other hand, when there is foreign matter on the surface of the photomask, the transmitted light is blocked by the foreign matter and the output becomes low, while the reflected light is scattered by the foreign matter and similarly the output becomes low. Therefore, by comparing a signal expressing the sum of the output of the transmitted image and the output of the reflected image with a threshold value, it is possible to detect the existence of foreign matter present on each die.

The output signal from the scan converter 85*b* expressing the transmitted image of the left side head and the output signal of the scan converter 85*c* expressing the transmitted image of the right side head are supplied to a first subtractor 89*a*, the transmitted light of the left side head and the transmitted light of the right side head are compared, and the output is supplied to a third differential amplifier 88*c* and compared with a threshold value. Further, the output signal from the scan converter 85*a* expressing the reflected image of the left side head and the output signal of the scan converter 85*d* expressing the reflected image of the right side head are supplied to a second subtractor 89*b*, the reflected light of the left side head and the reflected light of the right side head are compared, and the output is supplied to a fourth differential amplifier 88*d* and compared with a threshold value. For example, when there is a defect in the chrome light blocking pattern in one of the dies of the photomask, for example, when there is a light blocking pattern which should not be there or when there isn't a light blocking pattern which should be there, it is possible to detect a defect in the light blocking pattern by comparing the dies.

Further, in the above embodiment, use was made of a single mercury lamp and a single argon laser as the light source, but it is also possible to use a single mercury lamp and four optical fibers and divide the illumination light into four beams. Alternatively, it is possible to use four separate light sources.

In the above embodiment, the light beam from the laser light source was divided into two and the resultant beams deflected cyclically by individual acoustic optical elements, but it is also possible to deflect the light beam generated from a laser light source by a single acoustic optical element and then divide it into two.

While the invention has been described with reference to specific embodiments chosen for purpose of illustration, it should be apparent that numerous modifications could be made thereto by those skilled in the art without departing from the basic concept and scope of the invention.

For example, in the above embodiments, the explanation was given of the case of application to inspection of a photomask for defects, but the invention can also be applied to picking up an image of a pattern formed on various other types of substrates and inspecting for defects there. For example, the invention can also be applied as an image pickup apparatus for a pattern formed on the surface of a semi-conductor wafer during the process of production of a semi-conductor device or to a defect inspection system for various types of patterns formed on a semi-conductor wafer. Further, since the confocal optical system has a relatively short depth of focus, the invention may be applied to inspection of the flatness of the surface of the substrate etc. or warping of the substrate etc. Therefore, the invention can also be used for inspection of defects of samples not formed with patterns, for example, a photomask blank or semi-conductor wafer blank. Further, the invention may also be applied to inspection for defects of a substrate of a liquid crystal display.

The present disclosure relates to subject matter contained in Japanese Patent Application No. 2000-317587, filed on Oct. 18, 2000, the disclosure of which is expressly incorporated herein by reference in its entirety.

What is claimed is:

1. An image pickup apparatus comprising:
   a sample stage for moving a sample whose image is to be picked up in a first direction;
   an illumination light source for projecting illumination light on the sample;
   a first spatial filter arranged between the illumination light source and sample and having a plurality of slits formed at a predetermined pitch along the first direction and extending in a second direction perpendicular to said first direction;
   an image sensor for receiving reflected light or transmitted light from the sample, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;
   a second spatial filter arranged between the sample stage and the second image sensor and having a plurality of slits formed at a predetermined pitch along the first direction and extending in the second direction;
   an objective lens arranged between said sample stage and second spatial filter and forming an image of transmitted light or reflected light from the sample on the image sensor via the slits of the second spatial filter; and
   a drive control circuit for controlling the charge transfer speed of the image sensors and speed of movement of the sample stage;
   wherein, the first and second spatial filters are arranged so that light emitted from the slits of the first spatial filter strikes the sample and the image sensor through the slits of the second spatial filter.

2. An image pickup apparatus as set forth in claim 1, wherein the speed of movement of the sample stage and the charge transfer speed of the image sensor are set to correspond each other.

3. An image pickup apparatus as set forth in claim 1, wherein said illumination light source is a mercury lamp.

4. An image pickup apparatus as set forth in claim 3, wherein a wavelength filter is arranged between the mercury lamp and the first spatial filter.

5. An image pickup apparatus as set forth in claim 1, further comprising a position detection device for detecting a position of the sample stage in the first direction, said drive control circuit adjusting the charge transfer speed of said image sensor based on the stage position signal from said position detection device.

6. An image pickup apparatus comprising:
   a sample stage for moving a sample whose image is to be picked up in a first direction;
   a first light source for projecting illumination light for picking up a transmitted image of the sample;
   a second light source for projecting illumination light for picking up a reflected image of the sample;
   a first spatial filter arranged between said first light source and the sample stage and having a plurality of slits formed at a predetermined pitch along said first direction and extending in a second direction perpendicular to said first direction;
   a second spatial filter arranged between said second light source and the sample stage and having a plurality of slits formed at a predetermined pitch along the first direction and extending in the second direction perpendicular to the first direction;
   a first image sensor for receiving light generated from said first light source and passing through the sample, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;
   a second image sensor for receiving light generated from said second light source and reflected at the sample, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;
   a third spatial filter arranged between said sample stage and first image sensor and having a plurality of slits formed at a predetermined pitch along the first direction and extending in the second direction;
   a fourth spatial filter arranged between said sample stage and second image sensor and having a plurality of slits formed at a predetermined pitch along the first direction and extending in the second direction;
   an objective lens arranged between said sample stage and third and fourth spatial filters and forming an image of transmitted light and reflected light from the sample on the first and second image sensors via the slits of the third and fourth spatial filters, respectively; and
   a drive control circuit for controlling the charge transfer speed of the first and second image sensors and speed of movement of the sample stage;
   wherein, the first spatial filter and third spatial filter are arranged so that illumination light emitted from the slits of the first spatial filter strike the first image sensor through the sample, the objective lens and the slits of the third spatial filter;
   wherein, the second spatial filter and fourth spatial filter are arranged so that illumination light emitted from the slits of the second spatial filter strike the second image sensor through the sample, the objective and the slits of the fourth spatial filter.

7. An image pickup apparatus as set forth in claim 6, wherein the speed of movement of the sample stage and the charge transfer speed of the first and second image sensors are set to correspond each other.

8. An image pickup apparatus as set forth in claim 6, wherein said first and second light sources generate illumination light of same wavelengths and said third and fourth spatial filters are arranged so that the transmitted light from the sample strikes the light blocking portions between slits of the fourth spatial filter and the reflected light from the sample strikes the light blocking portions between the slits of the third spatial filter.

9. An image pickup apparatus as set forth in claim 6, wherein the wavelength of the illumination light generated from said first light source and the wavelength of the illumination light generated from the second light source are made different from each other and a separation element for separating the transmitted light and reflected light from the sample is arranged between the sample and the third and fourth spatial filters.

10. An image pickup apparatus comprising:
   a sample stage for moving a sample whose image is to be picked up in a first direction;
   a light source for generating a light beam;
   a diffraction grating for generating n number of sub beams at predetermined intervals along a direction corresponding to said first direction from said light beam;
   a beam deflection device for cyclically deflecting said sub beams by a predetermined frequency in a second direction perpendicular to said first direction;
   an image sensor for receiving reflected light or transmitted light from a sample, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;
   a spatial filter arranged between the sample stage and image sensor and having a plurality of slits formed at a predetermined pitch along the first direction and extending in the second direction;
   an objective lens arranged forming an image of transmitted light or reflected light from the sample on the image sensor via the slits of the second spatial filter; and
   a drive control circuit for controlling the drive of the image sensor and beam deflection apparatus;
   wherein, the reflected light or transmitted light of the plurality of sub beams scanning the surface of the sample strikes the image sensor through the slits of the spatial filter.

11. An image pickup apparatus comprising:
   a sample stage for moving a sample whose image is to be picked up in a first direction;
   a first light source for generating illumination light for picking up a transmitted image;
   a first spatial filter arranged between the illumination light source and the sample and having a plurality of slits formed at a predetermined pitch along said first direction and extending in a second direction perpendicular to said first direction;
   a first image sensor for receiving transmitted light from the sample, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;
   a second spatial filter arranged between the sample and first image sensor and having a plurality of slits formed at a predetermined pitch along the first direction and extending in the second direction;
   a second light source for generating a light beam for picking up a reflected image;
   a diffraction grating for generating n number of sub beams from the light beam;
   a beam deflection device for deflecting the sub beams by a predetermined frequency in a second direction perpendicular to the first direction;
   a second image sensor for receiving reflected light from a sample, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;
   a third spatial filter arranged between the sample stage and second image sensor and having a plurality of slits formed at a predetermined pitch along the first direction and extending in the second direction;
   an objective lens arranged forming an image of transmitted light and reflected light from the sample on the first and the second image sensors via the slits of the second and third spatial filter, respectively; and
   a drive control circuit for controlling the drive of the first and second image sensors and beam deflection apparatus;
   wherein, the first and second spatial filters are arranged so that the light emitted from the slits of the first spatial filter strike the first image sensor through the sample, the object lens and the slits of the second spatial filter;
   wherein, the third spatial filter is arranged so that the reflected light from the sample strikes the second image sensor through the object lens and the slits of the third spatial filter.

12. An image pickup apparatus as set forth in claim 11, wherein said first light source is a mercury lamp and said second light source is a laser.

13. An image pickup apparatus as set forth in claim 12, wherein a wavelength filter is arranged between the mercury lamp and the first spatial filter.

14. An image pickup apparatus comprising:
   a sample stage for moving a sample whose image is to be picked up in a first direction;
   an illumination light source for projecting illumination light for picking up a transmitted image;
   a first spatial filter arranged between the illumination light source and the sample and having a plurality of slits formed at a predetermined pitch along said first direction and extending in a second direction perpendicular to said first direction;
   a first image sensor for receiving transmitted light from the sample, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;

a second spatial filter arranged between the sample and first image sensor and having a plurality of slits formed at a predetermined pitch along the first direction and extending in the second direction;

a light source for generating a light beam for picking up a reflected image;

a beam deflection device for deflecting said light beam by a predetermined frequency in a second direction perpendicular to the first direction;

a linear image sensor for receiving the reflected light from said sample, having a plurality of light receiving elements arranged in a line along the second direction, and reading out the charges stored in the light receiving elements in synchronization with the first image sensor;

an objective lens arranged for forming images of transmitted light and reflected light from the sample on the first image sensor and the linear image sensor, respectively; and a drive control circuit for controlling the drive of the first and the linear image sensor and said beam deflection apparatus;

wherein, the first and second spatial filters being arranged so that the light emitted from the slits of the first spatial filter strikes the image sensor through the sample, the objective lens, and the slits of the second spatial filter.

15. An image pickup apparatus as set forth in claim 14, wherein said beam deflection apparatus is comprised by an acoustic optical device and the beam deflection frequency of the acoustic optical element is set to a whole multiple (including an equal value) of the charge transfer speed of the first image sensor.

16. An image pickup apparatus as set forth in any one of claim 14, wherein each light receiving element of said image sensors has a charge storing ability able to store a charge generated in accordance with light striking it.

17. A photomask defect inspection system comprising:

a sample stage for moving a photomask to be inspected for defects in a first direction;

a first light source for projecting illumination light on the photomask;

a first spatial filter arranged between said first light source and the sample stage and having a plurality of slits formed at a predetermined pitch along said first direction and extending in a second direction perpendicular to said first direction;

a first image sensor for receiving light generated from said first light source and passing through the photomask, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;

a third spatial filter arranged between said sample stage and first image sensor and having a plurality of slits formed at a predetermined pitch along the first direction and extending in the second direction;

a second light source for projecting illumination light on the photomask;

a third spatial filter arranged between said second light source and the sample stage and having a plurality of slits formed at a predetermined pitch along the first direction and extending in the second direction perpendicular to the first direction;

a second image sensor for receiving light generated from said second light source and reflected by the sample, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;

a fourth spatial filter arranged between said sample stage and second image sensor and having a plurality of slits formed at a predetermined pitch along the first direction and extending in the second direction;

an objective lens arranged between said sample stage and third and fourth spatial filters and forming images of transmitted light and reflected light from the sample on the first and second image sensors via the slits of the third and fourth spatial filters, respectively; and a drive control circuit for controlling the charge transfer speed of the first and second image sensors and speed of movement of the sample stage; and a defect detection circuit for detecting defects of the photomask based on the output signals of the first and second image sensors;

wherein, the first spatial filter and third spatial filter are arranged so that illumination light emitted from the slits of the first spatial filter strikes the first image sensor through the sample, the objective lens and the slits of the third spatial filter;

wherein, the second spatial filter and fourth spatial filter are arranged so that illumination light emitted from the slits of the second spatial filter strikes the second image sensor through the sample, the objective and the slits of the fourth spatial filter.

18. A photomask defect inspection system as set forth in claim 17, wherein the speed of movement of the sample stage and the charge transfer speed of the first and second image sensors are set to correspond each other.

19. A photomask defect inspection system as set forth in claim 17, wherein said first and second light sources generate illumination light of same wavelengths and said third and fourth spatial filters are arranged so that the transmitted light from the sample strikes the light blocking portions between slits of the fourth spatial filter and the reflected light from the sample strikes the light blocking portions between the slits of the third spatial filter.

20. A photomask defect inspection system as set forth in claim 17, wherein the wavelength of the illumination light generated from said first light source and the wavelength of the illumination light generated from the second light source are made different from each other and a separation element for separating the transmitted light and reflected light from the sample is arranged between the sample stage and the third and fourth spatial filters.

21. A photomask defect inspection system comprising:

a stage for moving a photomask to be inspected for defects in a first direction;

a first light source for projecting illumination light on the photomask, a first spatial filter arranged between the first light source and stage and having a plurality of slits formed at a predetermined pitch along said first direction and extending in a second direction perpendicular to said first direction;

a first image sensor for receiving transmitted light from the photomask, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;

a second spatial filter arranged between the stage and first image sensor and having a plurality of slits formed at a predetermined pitch along the first direction and extending in the second direction;

a second light source for generating a light beam;

a diffraction grating for generating n number of sub beams from the light beam at equal intervals along a direction corresponding to said first direction;

a beam deflection device for cyclically deflecting said sub beams by a predetermined frequency in a second direction perpendicular to said first direction;

a second image sensor for receiving reflected light from the photomask, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;

a third spatial filter arranged between the stage and second image sensor and having a plurality of slits extending in the second direction;

an objective lens for forming an image of transmitted light and reflected light from the sample on the first and second image sensors via the slits of the second and third spatial filters;

a drive control circuit for controlling the drive of the first and second image sensors and the beam deflection apparatus; and a defect detection circuit for detecting defects of the photomask based on the output signals of the first and second image sensors;

wherein, the first and second spatial filters are arranged so that the light emitted from the slits of the first spatial filter enters the slits of the second spatial filter;

wherein, the third spatial filter are arranged so that the reflected light of the plurality of sub beams scanning the surface of the photomask enters the slits of the third spatial filter.

22. A photomask defect inspection system as set forth in claim 21, wherein the first light source is a mercury lamp and the second light source is a laser.

23. A photomask defect inspection system as set forth in claim 21, wherein a wavelength filter is arranged between the mercury lamp and the first spatial filter.

24. A photomask defect inspection system as set forth in claim 22, wherein the wavelength of the light generated from said mercury lamp and the wavelength of the light generated from the laser are made different from each other and a separation element for separating the transmitted light and reflected light from the sample is arranged between the sample and the third and fourth spatial filters.

25. A photomask defect inspection system comprising:

a stage for moving a photomask to be inspected for defects in a first direction, first and second image pickup apparatuses for picking up an image of the photomask, and a defect detection circuit for detecting defects existing in a photomask based on output signals of the first and second image pickup apparatuses;

each of the first and second image pickup apparatuses being provided with:

an illumination light source for projecting illumination light on the photomask;

a first spatial filter arranged between the illumination light source and stage and having a plurality of slits formed at a predetermined pitch along said first direction and extending in a second direction perpendicular to said first direction;

a first image sensor for receiving transmitted light from the photomask, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;

a second spatial filter arranged between the stage and first image sensor and having a plurality of slits formed at a predetermined pitch along the first direction and extending in the second direction;

a light source for generating a light beam for picking up a reflected image;

a diffraction grating for generating n number of sub beams from the light beam at equal intervals along a direction corresponding to said first direction;

a beam deflection device for cyclically deflecting said sub beams by a predetermined frequency in a second direction perpendicular to said first direction;

a second image sensor for receiving reflected light from the photomask, having a plurality of light receiving elements arranged in a two-dimensional array along said first and second directions, successively transferring the charges stored in one line of light receiving elements arranged in the second direction for each line at a predetermined transfer speed, and successively outputting the charges stored in the light receiving elements;

a third spatial filter arranged between the stage and second image sensor and having a plurality of slits extending in the second direction;

an object lens for forming an image of transmitted light and reflected light from the sample on the first and second image sensors via the slits of the second and third spatial filters; and a drive control circuit for controlling the drive of the first and second image sensors and the beam deflection apparatus;

wherein, the first and second spatial filters being arranged so that the light emitted from the slits of the first spatial filter enter the slits of the second spatial filter;

wherein, the third spatial filter being arranged so that the reflected light of the plurality of sub beams scanning the surface of the photomask enters the slits of the third spatial filter.

26. A photomask defect inspection system as set forth in claim 25, wherein said defect detection circuit is provided with a comparison circuit for comparing output signals of the first and second image sensors of the first image pickup apparatus and output signals of the first and second image sensors of the second image pickup apparatus and defects are detected based on the results of the comparison circuit.

* * * * *